(12) United States Patent
Whitaker

(10) Patent No.: US 11,928,956 B2
(45) Date of Patent: *Mar. 12, 2024

(54) FINGERTIP MEDICAL VIBRATORY DEVICE

(71) Applicant: Elizabeth Whitaker, Marietta, GA (US)

(72) Inventor: Elizabeth Whitaker, Marietta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/481,659

(22) Filed: Sep. 22, 2021

(65) Prior Publication Data

US 2022/0005329 A1   Jan. 6, 2022

Related U.S. Application Data

(63) Continuation of application No. 16/429,849, filed on Jun. 3, 2019, now Pat. No. 11,132,878.

(60) Provisional application No. 62/679,266, filed on Jun. 1, 2018.

(51) Int. Cl.
| | |
|---|---|
| *G08B 6/00* | (2006.01) |
| *A61B 34/00* | (2016.01) |
| *A61B 42/10* | (2016.01) |

(52) U.S. Cl.
CPC ............ *G08B 6/00* (2013.01); *A61B 34/76* (2016.02); *A61B 42/10* (2016.02)

(58) Field of Classification Search
CPC ........ A61B 2090/064; A61B 2090/065; A61B 34/76; A61B 42/10; A61B 42/20; A61B 5/150137; A61H 2201/1215; A61H 2201/165; A61H 2201/5007; A61H 2201/5025; A61H 2201/5058; A61H 2205/067; A61H 23/0263; A61M 5/422; G08B 6/00

See application file for complete search history.

(56) References Cited

U.S. PATENT DOCUMENTS

| | | | |
|---|---|---|---|
| 2005/0245910 A1* | 11/2005 | Wright | A61F 9/00745 606/1 |
| 2014/0267116 A1* | 9/2014 | Weiner | A61F 5/05875 345/173 |
| 2017/0285848 A1* | 10/2017 | Rosenberg | G06F 3/04883 |
| 2018/0021099 A1* | 1/2018 | Warner | G06F 3/016 604/95.01 |
| 2020/0078260 A1* | 3/2020 | Choudhury | A61H 19/34 |

* cited by examiner

*Primary Examiner* — Quan Zhen Wang
*Assistant Examiner* — Rajsheed O Black-Childress
(74) *Attorney, Agent, or Firm* — Howard & Howard Attorneys PLLC

(57) ABSTRACT

An apparatus comprising a vibrating finger device useful in a medical setting includes a device body configured to fit on a finger of a wearer, a vibrating unit, a touch sensitive sensor, and a control module including a computerized processor. The control module includes programming configured to monitor an activation input to the device, determine the monitored activation input to indicate a threshold desired vibration activation input, and activate a vibration cycle within the vibrating unit based upon the determination.

16 Claims, 8 Drawing Sheets

FINGERTIP MEDICAL VIBRATORY DEVICE

CROSS-REFERENCE TO RELATED APPLICATIONS

This disclosure is a continuation of U.S. patent application Ser. No. 16/429,849 filed on Jun. 3, 2019 and claims priority to U.S. Provisional Patent Application No. 62/679,266 filed on Jun. 1, 2018, which is hereby incorporated by reference.

TECHNICAL FIELD

This disclosure is related to a finger device useful to provide a vibratory input to skin brought in proximity to the device, in particular, to a device configured to be worn under medical gloves.

BACKGROUND

The statements in this section merely provide background information related to the present disclosure. Accordingly, such statements are not intended to constitute an admission of prior art.

Doctors and other medical personnel sometimes seek to lessen the pain associated with injections and another needle pricks that patients must endure. One method to lessen this pain is through tactile stimulation or by pressing a finger into the area that is about to be pricked and move the finger vigorously for a few seconds. This stimulation by the doctor's finger, under a theory of pain known as the gate control theory, causes the nerves in the area to send intense touch signals to the brain. This sudden touch stimulation partially overloads the brain's ability read nerve inputs from that area of the skin, such that when a hypodermic needle is subsequently injected in that skin, the sensation related to the needle prick that is input by the brain is less intense than it would be without the prior stimulation.

Finger vibratory devices are known, in particular, related to adult/intimacy products. Such products are put upon a fingertip, and when pressure is applied to the fingertip, a circuit is activated creating a vibration in the fingertip device. While such a device could be useful for tactile stimulation, a device such as that would be unsanitary or unsterile for use in a medical environment. Testing has shown that such devices, when a medical glove is put on over the device, tends to stay on due to the constant pressure that the glove puts on the finger and device or tends to turn on every time that the doctor's hand touches any object.

SUMMARY

An apparatus including a vibrating finger device useful in a medical setting is provided and includes a device body configured to fit on a finger of a wearer, a vibrating unit, a touch sensitive sensor, and a control module including a computerized processor. The control module includes programming configured to monitor an activation input to the device, determine the monitored activation input to indicate a threshold desired vibration activation input, and activate a vibration cycle within the vibrating unit based upon the determination.

According to one or more embodiments, the control module including the computerized processor includes a circuit board.

According to one or more embodiments, the device is configured to be worn under a medical glove.

According to one or more embodiments, the touch sensitive sensor is located at a tip of the device body, and the vibrating unit is located at the tip of the device body.

According to one or more embodiments, the touch sensitive sensor is located on a back side of the device body, the vibrating unit is located on the back side of the device body, the control module including the computerized processor includes a circuit board, and the circuit board is located on the back side of the device body.

According to one or more embodiments, the programming configured to activate the vibration cycle includes programming configured to control the vibration cycle at a constant vibration magnitude.

According to one or more embodiments, the programming configured to activate the vibration cycle includes programming configured to control the vibration cycle at a constant vibration magnitude.

According to one or more embodiments, the programming configured to activate the vibration cycle includes programming configured to control the vibration cycle with a vibration magnitude escalating over time.

According to one or more embodiments, the programming configured to activate the vibration cycle includes programming configured to control the vibration cycle with a vibration magnitude oscillating over time.

According to one or more embodiments, the programming configured to monitor the activation input includes programming configured to monitor the touch sensitive sensor.

According to one or more embodiments, the control module further includes programming configured to control parameters of the vibration cycle based upon monitoring the touch sensitive sensor.

According to one or more embodiments, the control module further includes programming configured to select one of a plurality of vibration programs based upon monitoring the touch sensitive sensor.

According to one or more embodiments, the apparatus further includes an on/off switch, and the programming configured to monitor the activation input includes programming configured to monitor the on/off switch. According to one or more embodiments, the control module further includes programming configured to monitor the touch sensitive sensor as a secondary input. According to one or more embodiments, the programming configured to activate the vibration cycle includes programming configured to authorize the vibration cycle based upon the monitored activation input exceeding the threshold desired vibration activation input, and programming configured to trigger the vibration cycle based upon the secondary input. According to one or more embodiments, the control module further includes programming configured to control one of a duration and intensity of the vibration cycle based upon the secondary input. According to one or more embodiments, the control module further includes programming configured to select one of a plurality of vibration programs based upon the secondary input.

An apparatus including a vibrating finger device useful in a medical setting is provided and includes a device body configured to fit on a finger of a wearer, a vibrating unit, a touch sensitive sensor, and a circuit board. The circuit board includes programming configured to monitor the touch sensitive sensor, determine the monitored touch sensitive sensor to indicate a threshold desired vibration activation input, and activate a vibration cycle within the vibrating unit based upon the determination. The device is configured to be worn under a medical glove.

BRIEF DESCRIPTION OF THE DRAWINGS

One or more embodiments will now be described, by way of example, with reference to the accompanying drawings, in which.

DETAILED DESCRIPTION

A vibratory fingertip device is provided for use in medical environments, wherein a computerized processor within the device monitors inputs to the device, determines a threshold desired vibration activation input, and activates a vibration cycle based upon the determination. Devices in the art that simply vibrate when a touch sensitive sensor is activated are not useful in a medical environment because a doctor cannot tolerate a device that unintentionally vibrates every time an incidental contact is made. The disclosed device is useful under known medical gloves, and the device includes hardware and/or software to prevent accidental or incidental activation of the vibration feature outside of the desired tactile stimulation function.

Figure 1:
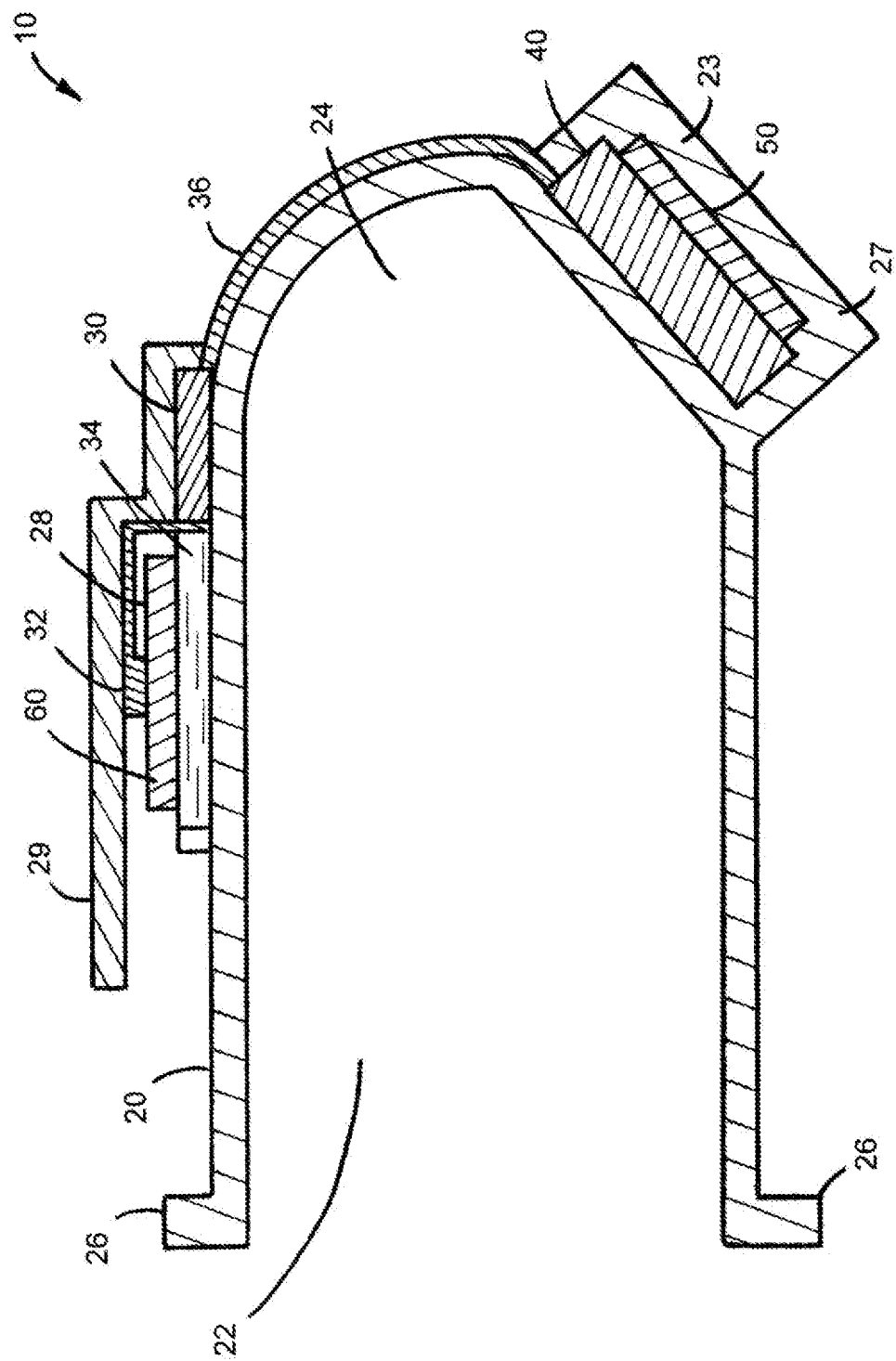
FIG. 1 illustrates an exemplary vibratory fingertip device in side sectional view, in accordance with the present disclosure.

Referring now to the drawings, wherein the showings are for the purpose of illustrating certain exemplary embodiments only and not for the purpose of limiting the same, FIG. 1 illustrates an exemplary vibratory fingertip device in side sectional view. Any number of physical arrangements or alternative equivalent components for the illustrated device are envisioned, and the disclosure is not intended to be limited to the exemplary embodiment of FIG. 1. FIG. 1 illustrates fingertip device 10 including polymerized, flexible device body 20 including fingertip shaped cavity 22. Tip 24 includes a touch sensitive sensor 50 may be configured to measure pressure applied by the finger of the wearer upon proximate surfaces such as the skin of a patient. Tip 24 also includes vibration unit 40 which can include a small motor and off-center weight, such that when the motor spins, the off-center weight causes the device to vibrate. Touch sensitive sensor 50 and vibration unit 40 can be fully encapsulated within surface 23 of body 20. A computerized processor is provided within exemplary circuit board 30. Vibration unit 40 can be electronically connected though wire bundle 36 to circuit board 30 which includes coded programming and/or functionality to control vibration of vibration unit 40 based upon monitored force inputs from touch sensitive sensor 50. Circuit board 30 can be connected to exemplary round wrist-watch-style battery 60 through electrodes 32 and 34. Electrode 34 includes spring-activated conductive bracket 28 which aids in holding battery 60 in place. Body 20 includes flap 29 configured to cover battery 60 and further includes annular ring 26 configured to prevent the bottom of body 20 from rolling up upon the finger of the user. Surface 23 includes flat end 27 configured to be placed squarely next to the skin of the user such that accurate force readings can be measured by touch sensitive sensor 50.

Touch sensitive sensor 50 can act as an activation input or an input used to determine whether a vibration cycle should be activated, with the device monitoring pressure applied to the touch sensitive sensor 50 and determining a desire to activate a vibration cycle based upon the activation input. In determining whether inputs to the device through the activation input do indicate the desire to activate a vibration cycle, the inputs to the device are compared to a programmed threshold or a threshold desired vibration activation input, and if the inputs exceed the threshold desired vibration activation input, then the vibration cycle can be activated. Other inputs in place of a touch sensitive sensor can be used as an activation input, for example, including an on/off switch. In such an embodiment, a touch sensitive sensor can be used as a secondary input, for example, providing control parameters for the vibration cycle to be performed or triggering the already activated vibration cycle.

Touch sensitive sensor 50 can include any of a wide variety of touch sensors in the art or sensor capable of measuring pressure applied by or touching contact of a finger of a wearer through the disclosed vibratory fingertip device. In one embodiment, touch sensitive sensor 50 can include a wire resistive sensor, wherein electrical resistance of a circuit can be changed or a previously open circuit can be closed based upon force applied to the sensor. In another embodiment, touch sensitive sensor 50 can include an infrared sensitive sensor.

A computerized processor is provided within exemplary circuit board 30. Circuit board 30 includes hardware in the art configured to perform computerized functionality. In the present device, circuit board 30 utilizes programmed code to monitor inputs to the device, either to a touch sensitive sensor and/or an on/off switch to determine when a doctor or user intend the device initiate a vibration cycle. The computerized processor within the device illustrated in FIG. 1 monitors inputs the device, in particular, inputs to the touch sensitive sensor, determines a threshold desired vibration activation input, and activates a vibration cycle based upon the determination.

Figure 2:
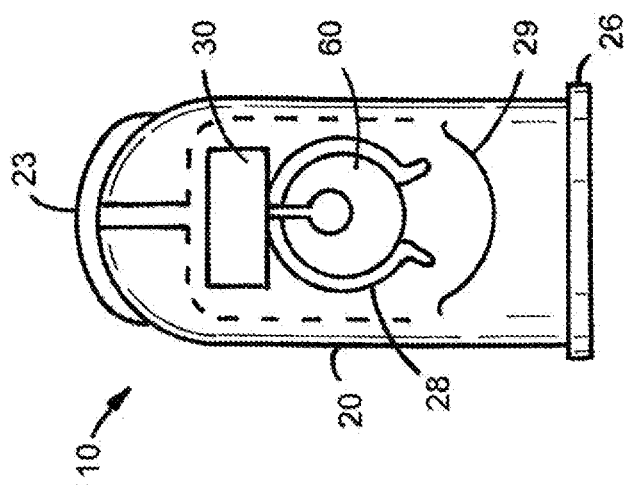
FIG. 2 illustrates the vibratory fingertip device of FIG. 1 from a top view, in accordance with the present disclosure.

FIG. 2 illustrates the vibratory fingertip device of FIG. 1 from a top view. Device 10 is illustrated including body 20 including annular ring 26, circuit board 30, battery 60, spring-activated conductive bracket 28, flap 29, and surface 23.

Figure 3:
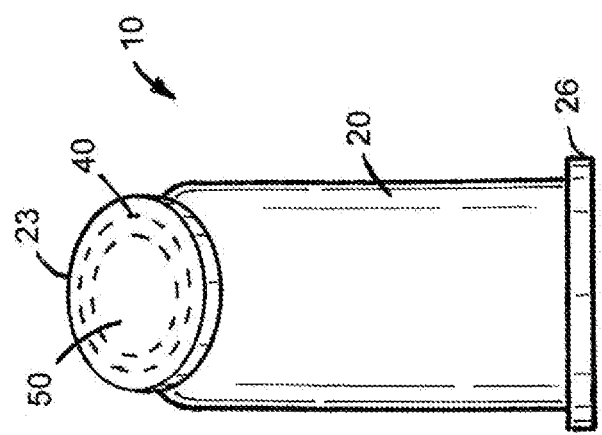
FIG. 3 illustrates the vibratory fingertip device of FIG. 1 from a bottom view, in accordance with the present disclosure.

FIG. 3 illustrates the vibratory fingertip device of FIG. 1 from a bottom view. Device 10 is illustrated including body 20 including annular ring 26, surface 23, vibration unit 40, and touch sensitive sensor 50.

Body 20 of the device may be constructed of various different polymerized materials, the material may have various different durometers, and the device may have different dimensions from the illustrated examples.

Figure 4:
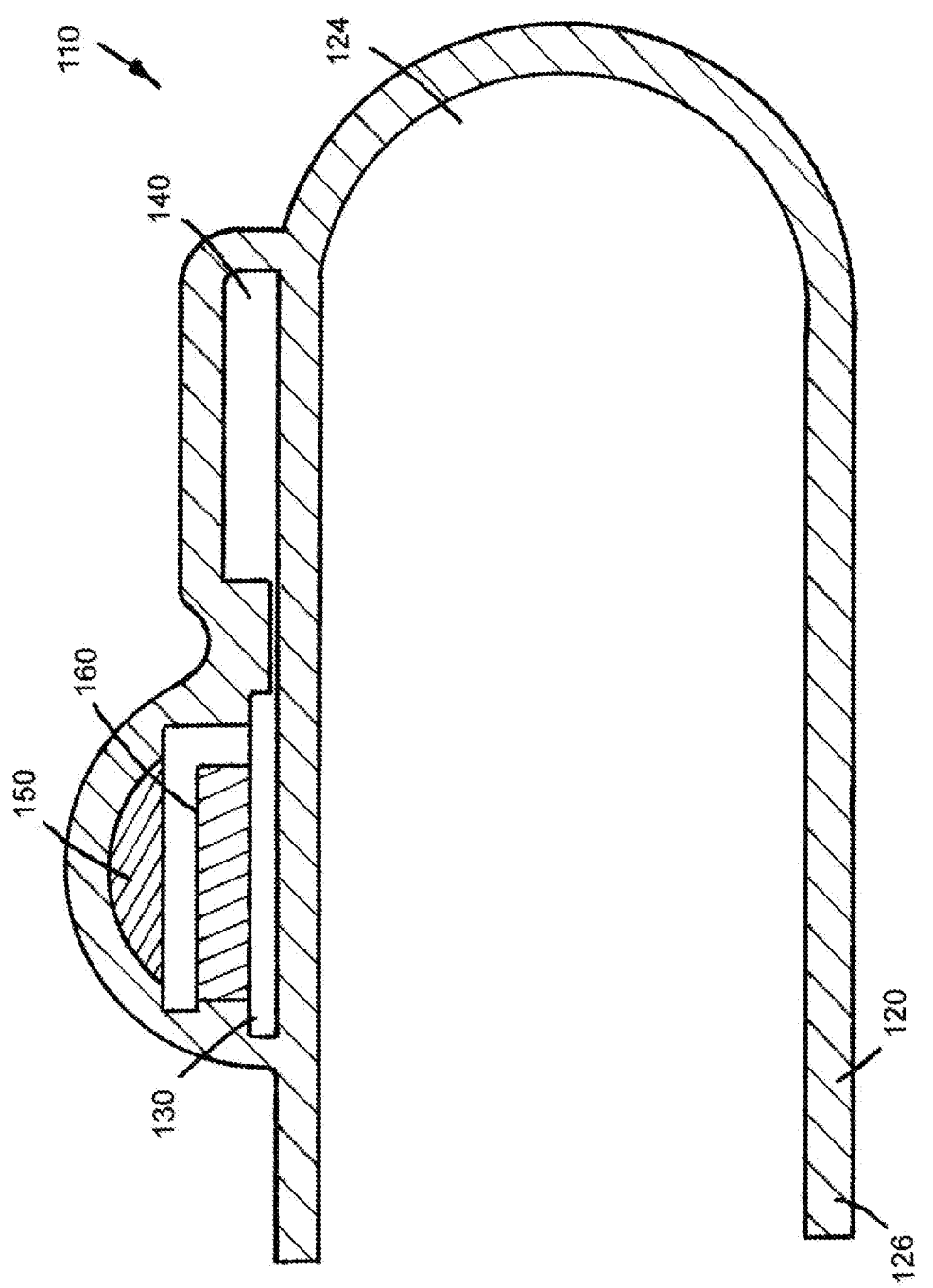
FIG. 4 illustrates an alternative exemplary vibratory fingertip device in side sectional view, in accordance with the present disclosure.

FIG. 4 illustrates an alternative exemplary vibratory fingertip device in side sectional view. Device 110 is illustrated including flexible device body 120 including a fingertip shaped cavity with tip 124. A vibration unit 140, circuit board 130, battery 160, and activation button 150 are illustrated on a back or upper side of the device, with no vibration features located on a tip of device 110. Activation button 150 can be described as a touch sensitive sensor similar to the touch sensitive sensor of FIG. 1. End 126 of body 120 is illustrated without an annular ring in order to facilitate easy use, easy taking off and putting on of medical gloves without the device hanging up on the rubberized surface of the glove. Device 110 permits a doctor to use her hand normally, with no electronic devices between the fingertip and the patient's skin. When the doctor wants to activate the tactile stimulation feature, the doctor can hit button 150, bend her finger, and press vibration device 140 against the skin of the patient. In one exemplary use, the doctor can press button 150, and the vibration device can be activated 3 seconds later to vibrate for 10 subsequent seconds.

The computerized processor within the device illustrated in FIG. 4, embodied as circuit board 130, monitors inputs to the device, in particular, inputs to the touch sensitive sensor, determines a threshold desired vibration activation input, and activates a vibration cycle based upon the determination.

Figure 5:
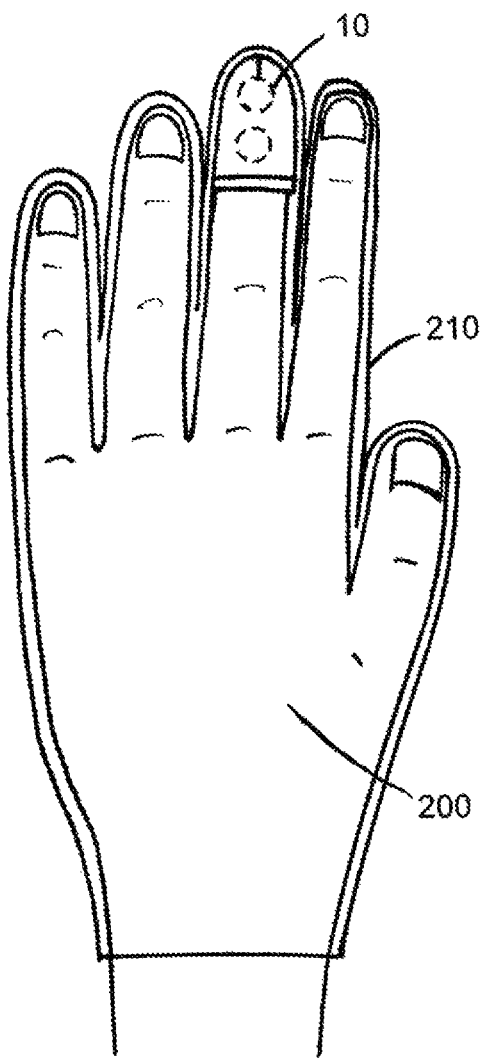
FIG. 5 illustrates the vibratory fingertip device of FIG. 4 situated upon a finger of a user with a medical glove worn over the device, in accordance with the present disclosure.

FIG. 5 illustrates the vibratory fingertip device of FIG. 4 situated upon a finger of a user with a medical glove worn over the device. Hand 200 is illustrated with device 10 installed to the middle finger of the user. Glove 210 is illustrated worn over device 10.

Figure 6:
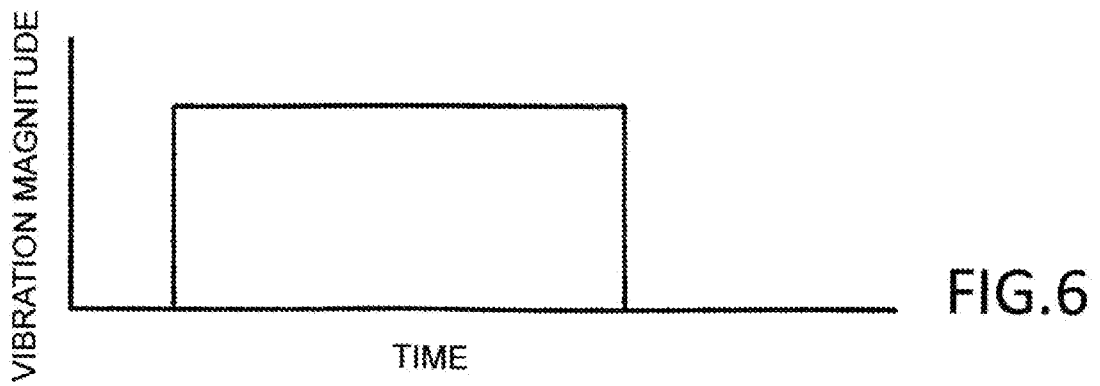
FIGS. 6-8 illustrate exemplary vibration profiles that can be used to control either or both the vibration magnitude and frequency of the vibration provided by the disclosed devices, in accordance with the present disclosure.
Figure 7:
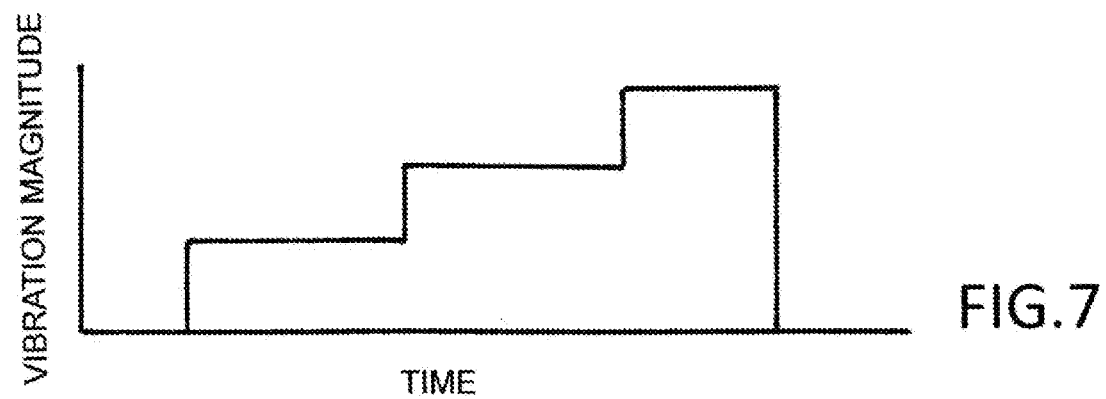
Figure 8:
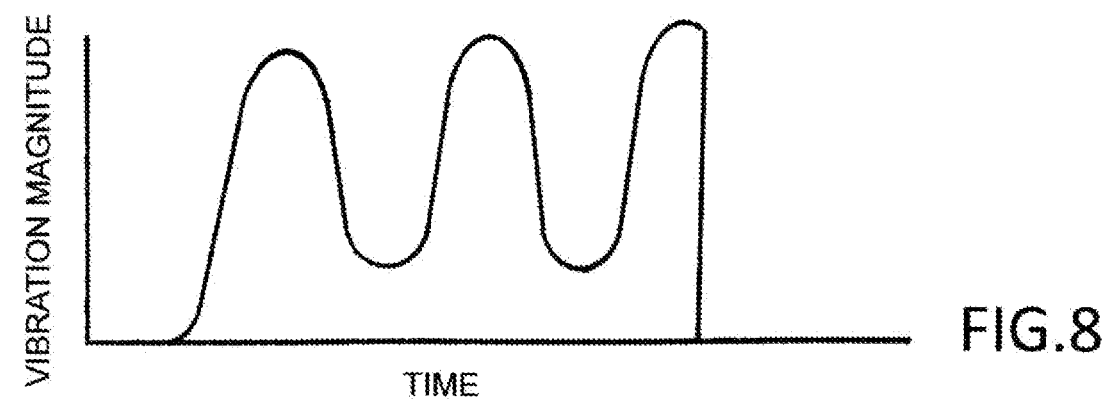

FIGS. 6-8 illustrate exemplary vibration profiles that can be used to control either or both the vibration magnitude and frequency of the vibration provided by the disclosed devices. FIG. 6 illustrates exemplary vibration magnitude on a vertical axis and time on a horizontal axis. A constant vibration magnitude is shown for some time period. FIG. 7 illustrates exemplary vibration magnitude on a vertical axis and time on a horizontal axis. FIG. 7 illustrates the vibration magnitude escalating over time. An increasing magnitude, increasing in steps, is illustrated, over a time period. In other examples, the magnitude can increase gradually. FIG. 8 illustrates exemplary vibration magnitude on a vertical axis and time on a horizontal axis. The magnitude of the vibration changes or oscillates over time in an exemplary sinusoidal form, with the magnitude oscillating up and down over the illustrated time period. The oscillation could in other examples include step-form oscillations. FIGS. 6-8 are exemplary, and the disclosure is not intended to be limited to the particular examples provided.

The computerized processor of the disclosed device can monitor inputs to the device and determine whether the monitored inputs indicate a threshold desired vibration activation input. An on-off switch can provide an input to the device useful to determine whether the monitored inputs indicate a threshold desired vibration activation input. In another embodiment, inputs to the touch sensitive sensor of the device can be useful to determine whether the monitored inputs indicate a threshold desired vibration activation input. For example, pressure applied to the touch sensitive sensor may be required to be applied constantly for a set time period or duration, for example, 3, 4, or 5 seconds in order to that constant pressure to indicate a threshold desired vibration activation input. In another example, a rapid repeated inputs to the touch sensitive sensor, for example, three tapping inputs within one second or one and a half seconds, may be required in order to that constant pressure to indicate a threshold desired vibration activation input. In another example, a constant pressure for a required duration followed by a tapping input or a number of tapping inputs may be required in order for the inputs to indicate a threshold desired vibration activation input.

In one exemplary embodiment, the computerized process may be equipped to run two or more different vibration cycles, for example, of different duration or intensity, and inputs to the touch sensitive sensor may enable activation of the different alternative vibration cycles based upon the inputs to the touch sensitive sensor. For example, an input of a required duration may be required to "arm" the device, and then a number of tapping inputs within an activation duration may be required to select a vibration program. For example, a computerized processor could include code to monitor inputs from a touch sensitive sensor, "arm" the system based upon receiving a constant pressure input of at least two seconds, and then activate a first vibration cycle if one tapping input is monitored within three seconds of arming, alternatively activate a second vibration cycle if two tapping inputs are monitored within three seconds of arming, and alternatively activate a third vibration cycle if three tapping inputs are monitored within three seconds of arming. If no tapping inputs are monitored within the three second activation duration, then the system "disarms."

A number of different processes for monitoring a touch sensitive sensor and determining that the inputs indicate a threshold desired vibration activation input are envisioned, and the disclosure is not intended to be limited to the examples provided herein.

Figure 9:
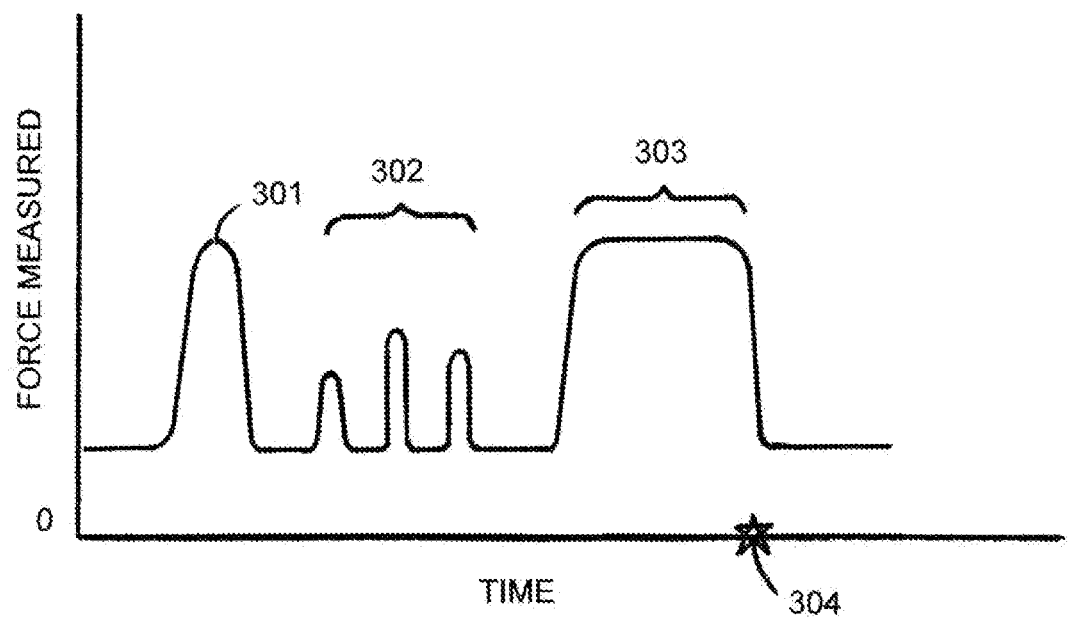
FIGS. 9 and 10 illustrate exemplary force input filtration and selective activation techniques, in accordance with the present disclosure.
Figure 10:
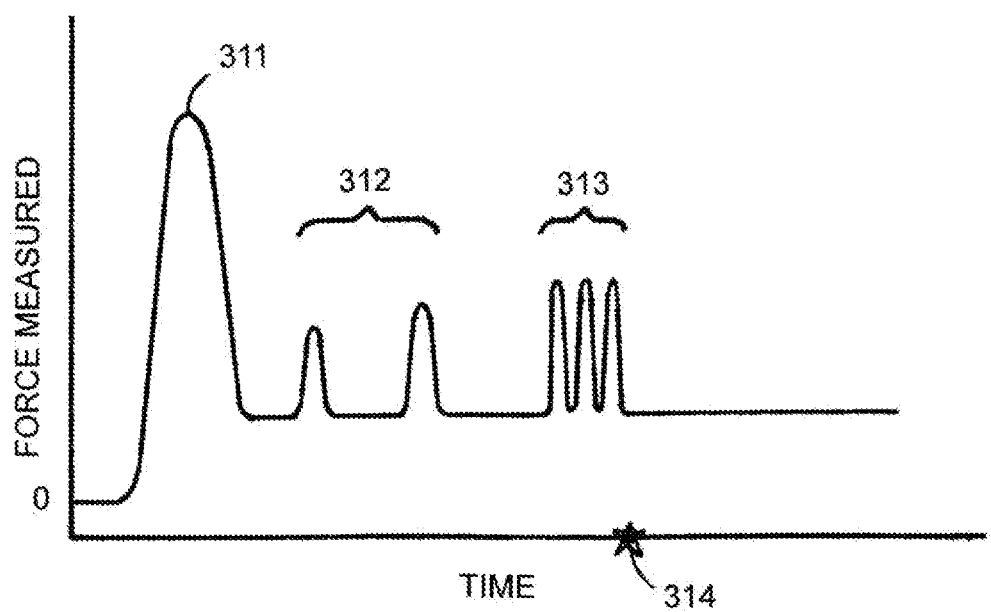

FIGS. 9 and 10 illustrate exemplary force input filtration and selective activation techniques useful to determine that the inputs indicate a threshold desired vibration activation input. Accidental or incidental activation of the vibration feature of the disclosed devices can be adverse to use in a medical environment. Patients can be unnecessarily startled by an unintended vibration, and a doctor can be distracted by an unintended vibration. FIG. 9 illustrates a force measured by a fingertip sensor on the device on a vertical axis and time on a horizontal axis. FIG. 9 can illustrate a computerized processor programmed to look for a constant input of at least a minimum duration to activate the device. Peak 301 illustrates a significant input of force applied to the sensor, however this input of force is not of sufficient duration to activate a vibration cycle. Peaks 302 illustrate small, intermittent force inputs to the sensor which can be consistent with normal use of the user's hand. Peak 303 shows a threshold force applied substantially consistently through a time period in excess of the minimum duration to activate the device. The disclosed devices can be programmed to activate only when the doctor presses the device against skin of a patient for a set duration, for example, for five seconds. Star 304 indicates a time that a vibration event can be initiated based upon the input meeting the criteria of a desired vibration event. FIG. 10 illustrates a force measured by a fingertip sensor on the device on a vertical axis and time on a horizontal axis. The plot of force starts at zero, for example, with the doctor activating the device before a glove is placed over the device. FIG. 10 can illustrate a computerized processor programmed to look for a threshold plurality of tapping inputs within a duration or period of time. Peak 311 illustrates a sharp peak of force applied to the sensor which can be consistent with placing a glove on the hand of the user. Even though peak 311 is substantial in magnitude, indicating that a large force was applied to the touch sensitive sensor, peak 311 does not meet the programmed criteria of the computerized processor of FIG. 10. Peaks 312 illustrate small, intermittent force inputs to the sensor which can be consistent with normal use of the user's hand, but peaks 312 do not meet the programmed criteria of the computerized processor of FIG. 10. Peaks 313 illustrate three sequential force inputs or tapping inputs which can be used to indicate the desire of the doctor that a vibration event should occur. Star 314 indicates a time that a vibration event can be initiated based upon the input meeting the criteria of a desired vibration event. FIGS. 9 and 10 are exemplary, and the disclosure is not intended to be limited to the particular examples provided.

Embodiments of the disclosure are described as being useful for use under medical gloves. Such use is advantageous because the medical glove provides a seal against contamination or intrusion of bacteria or other organisms that could be found in a medical treatment setting. However, embodiments of the disclosed device can be used without medical gloves. For example, the embodiment of FIG. 4 is sealed, with all electronic elements being encased in the rubberized or polymer material of the device body. Similarly, the device of FIG. 1 can include a seal or adhesive sealing the battery and other internal components such that the internal electronic mechanisms were entirely encased. In such a case where the device is entirely encased within a rubberized or polymer material, it can be appreciated that such a device could be used upon the hand of a person with hand sanitizer or other treatment being available to sanitize the device and keep it in an acceptable state for use in a medical setting.

Figure 11:
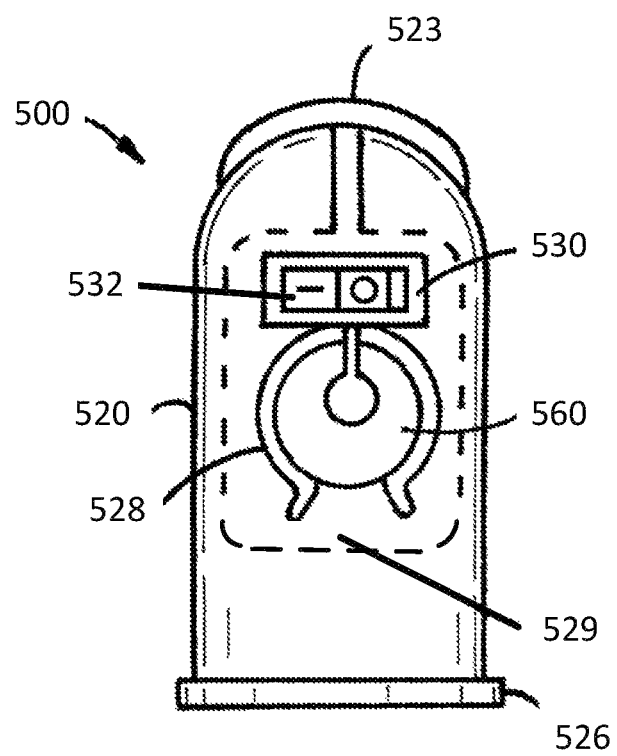
FIG. 11 illustrates an alternative exemplary vibratory fingertip device in top view, in accordance with the present disclosure.

FIG. 11 illustrates an alternative exemplary vibratory fingertip device in top view. The device of FIG. 11 is similar to the device of FIG. 1, except that on/off switch 532 is attached or electronically connected to circuit board 530. Device 500 is illustrated including body 520 including annular ring 526, circuit board 530, battery 560, spring-activated conductive bracket 528, and surface 523. Surface 523 covers a touch sensitive sensor and a vibration unit in accordance with the disclosure. In place of a flap covering the electronics of device 500, a cover 529 is attached to body 520 around a perimeter illustrated by a dotted line. The attachment of cover 529 can be performed through heat bonding, adhesive, or any other joining method in the art. In another embodiment, cover 529 can be formed integrally with body 520, with the other components being placed within a formation mold as the material for body 520 and cover 529 are initially provided.

On/off switch can be exposed through cover 529 or can be covered by cover 529. Cover 529 may soft enough and may be transparent or translucent such that the user can see the switch and activate it through cover 529.

In the embodiments of FIGS. 1 and 4, the device can monitor an activation input including monitoring pressure inputs to the touch sensitive sensor to determine appropriate activation of a vibration cycle. In such embodiments, the touch sensitive device can act as both an activation input and as a secondary input, for example, permitting later triggering of the vibration cycle or the user to control parameters such as duration or intensity of the vibration cycle. In another embodiment, the on/off switch of FIG. 11 can be the activation input for the device. The device can then take a secondary input or control input from the touch sensitive sensor, for example, receiving a second input, for example, controlling one of a duration or intensity of the vibration cycle. In another embodiment, after the activation input from the on/off switch is received, the unit can be primed to activate the vibration cycle as soon as a pressure input is received through the touch sensitive sensor. In this example, activation of the vibration cycle can be said to include two steps, one, the input to the activation input authorizes the vibration cycle, and, two, the input to the secondary input triggers the vibration cycle.

It will be appreciated that other similar embodiments of the disclosed invention can include an activation input without requiring use of a touch-sensitive sensor. For example, an on/off button can be used, where the device is programmed to vibrate for fifteen seconds after the on/off button is activated. In another example, the device can be programmed to activate a vibration cycle based upon monitoring a voice input to a microphone connected to the circuit board. Other activation inputs not related to a touch sensitive sensor are envisioned and the disclosure is not intended to be limited to the examples provided herein.

Figure 12:
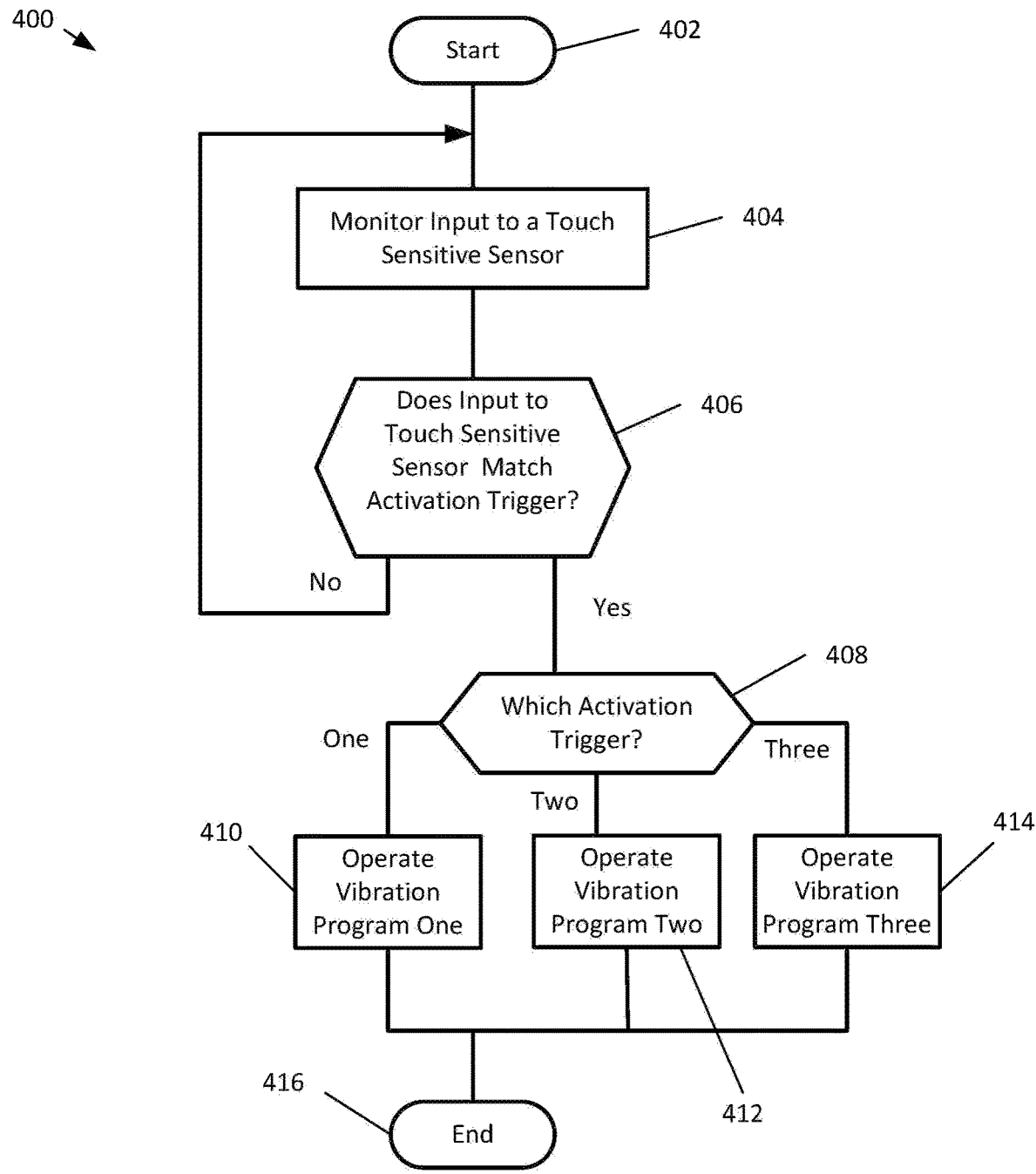
FIG. 12 is a flowchart illustrating an exemplary process to activate one of a plurality of vibration cycles, in accordance with the present disclosure.

FIG. 12 is a flowchart illustrating an exemplary process to activate one of a plurality of vibration cycles. Process 400 starts at step 402. At step 404, the device, or particularly a computerized processor of the device, monitors input to a touch sensitive sensor of the device. At step 406, the computerized processor determines whether the input to the touch sensitive sensor matches an activation trigger indicating a threshold desired vibration activation input. If no monitored input matches the activation trigger, the process returns to step 404. If the monitored input does match the activation trigger, the process advances to step 408, where the computerized processor determines whether the activation trigger indicates desired activation of vibration program one, vibration program two, or vibration program three. If the activation trigger indicates desired activation of vibration program one, the process advances to step 410 where vibration program one is operated. If the activation trigger indicates desired activation of vibration program two, the process advances to step 412 where vibration program two is operated. If the activation trigger indicates desired activation of vibration program three, the process advances to step 414 where vibration program three is operated. At step 416, the process ends. Process 400 is exemplary, and the disclosure is not intended to be limited to the exemplary process steps illustrated herein.

In one embodiment, a secondary input can be utilized to select between a plurality of vibration programs.

The disclosure has described certain preferred embodiments and modifications of those embodiments. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A system comprising a vibrating finger device useful in a medical setting, comprising:
   the vibrating finger device, including:
      a device body configured to fit on a finger of a wearer;
      a vibrating unit;
      a touch sensitive sensor; and
      a control module comprising a computerized processor, including programming configured to:
         monitor an input to the touch sensitive sensor as an activation input to the device;
         determine the monitored activation input to indicate a threshold desired vibration activation input; and
         activate a vibration cycle within the vibrating unit based upon the determination; and a medical glove fitted over the vibrating finger device; and wherein the device includes an arcuate exterior surface configured to for ease of use under the medical glove;

wherein the threshold desired vibration activation input is configured to enable the medical glove to be put on or removed without activating the vibration cycle;

wherein a shape of the device body enables taking off and putting on of the medical glove without the vibrating finger device hanging up on a surface of the medical glove; and wherein at least one of the vibrating unit and the touch sensitive sensor is disposed upon the device body.

2. The system of claim 1, wherein the control module comprising the computerized processor comprises a circuit board.

3. The system of claim 1, wherein the touch sensitive sensor is located at a tip of the device body; and
wherein the vibrating unit is located at the tip of the device body.

4. The system of claim 1, wherein the touch sensitive sensor is located on a back side of the device body;
wherein the vibrating unit is located on the back side of the device body;
wherein the control module comprising the computerized processor comprises a circuit board; and
wherein the circuit board is located on the back side of the device body.

5. The system of claim 1, wherein the programming configured to activate the vibration cycle comprises programming configured to control the vibration cycle at a constant vibration magnitude.

6. The system of claim 1, wherein the programming configured to activate the vibration cycle comprises programming configured to control the vibration cycle with a variable vibration magnitude.

7. The system of claim 1, wherein the programming configured to activate the vibration cycle comprises programming configured to control the vibration cycle with a vibration magnitude escalating over time.

8. The system of claim 1, wherein the programming configured to activate the vibration cycle comprises programming configured to control the vibration cycle with a vibration magnitude oscillating over time.

9. The system of claim 1, wherein the control module further includes programming configured to control parameters of the vibration cycle based upon monitoring the touch sensitive sensor.

10. The system of claim 1, wherein the control module further includes programming configured to select one of a plurality of vibration programs based upon monitoring the touch sensitive sensor.

11. The system of claim 1, further comprising an on/off switch in addition to the touch sensitive sensor and configured to prevent accidental activation of the vibrating finger device.

12. The system of claim 11, wherein the control module further includes programming configured to monitor the touch sensitive sensor as a secondary input.

13. The system of claim 12, wherein the programming configured to activate the vibration cycle comprises:
programming configured to authorize the vibration cycle based upon the monitored activation input exceeding the threshold desired vibration activation input; and
programming configured to trigger the vibration cycle based upon the secondary input.

14. The system of claim 12, wherein the control module further includes programming configured to control one of a duration and intensity of the vibration cycle based upon the secondary input.

15. The system of claim 12, wherein the control module further includes programming configured to select one of a plurality of vibration programs based upon the secondary input.

16. A system comprising a vibrating finger device useful in a medical setting, comprising:
the vibrating finger device, including:
a device body configured to fit on a finger of a wearer;
a vibrating unit;
a touch sensitive sensor; and
a circuit board, including programming configured to:
monitor the touch sensitive sensor;
determine the monitored touch sensitive sensor to indicate a threshold desired vibration activation input; and
activate a vibration cycle within the vibrating unit based upon the determination; and
a medical glove fitted over the vibrating finger device; and
wherein the device includes an arcuate exterior surface configured to for ease of use under the medical glove; and
wherein the threshold desired vibration activation input is configured to enable the medical glove to be put on or removed without activating the vibration cycle;
wherein the touch sensitive sensor is located at a tip of the device body;
wherein the vibrating unit is located at the tip of the device body; and
wherein a shape of the device body enables taking off and putting on of the medical glove without the vibrating finger device hanging up on a surface of the medical glove.

* * * * *